(12) United States Patent
Pipenhagen et al.

(10) Patent No.: US 7,621,937 B2
(45) Date of Patent: Nov. 24, 2009

(54) VASCULAR SEALING DEVICE WITH HIGH SURFACE AREA SEALING PLUG

(75) Inventors: Catherine A. Pipenhagen, Chanhassen, MN (US); Kedar R. Belhe, Minnetonka, MN (US); John Avi Roop, Crystal, MN (US)

(73) Assignee: St. Jude Medical Puerto Rico LC, Caguas, PR (US)

( * ) Notice: Subject to any disclaimer, the term of this patent is extended or adjusted under 35 U.S.C. 154(b) by 217 days.

(21) Appl. No.: 10/726,966

(22) Filed: Dec. 3, 2003

(65) Prior Publication Data

US 2005/0125031 A1 Jun. 9, 2005

(51) Int. Cl.
*A61B 17/04* (2006.01)
*A61B 17/08* (2006.01)
(52) U.S. Cl. ...................................... 606/232; 606/213
(58) Field of Classification Search ................. 606/232, 606/213, 72, 95, 215, 151, 76; 424/423
See application file for complete search history.

(56) References Cited

U.S. PATENT DOCUMENTS

| | | | |
|---|---|---|---|
| 4,317,445 A | 3/1982 | Robinson | |
| 4,744,364 A | 5/1988 | Kensey | 128/334 |
| 4,890,612 A | 1/1990 | Kensey | |
| 5,021,059 A | 6/1991 | Kensey et al. | 606/213 |
| 5,061,274 A | 10/1991 | Kensey | 606/213 |
| 5,108,421 A | 4/1992 | Fowler | |
| 5,116,357 A * | 5/1992 | Eberbach | 606/213 |
| 5,192,302 A | 3/1993 | Kensey et al. | 606/213 |
| 5,222,974 A | 6/1993 | Kensey et al. | 606/213 |
| 5,282,827 A | 2/1994 | Kensey et al. | |
| 5,290,310 A | 3/1994 | Makower et al. | |
| 5,292,332 A | 3/1994 | Lee | |
| 5,304,184 A | 4/1994 | Hathaway et al. | |
| 5,306,254 A | 4/1994 | Nash et al. | |
| 5,312,435 A | 5/1994 | Nash et al. | 606/213 |
| 5,320,639 A | 6/1994 | Rudnick | |
| 5,326,350 A | 7/1994 | Li | |
| 5,334,216 A | 8/1994 | Vidal et al. | 606/213 |
| 5,342,393 A | 8/1994 | Stack | |
| 5,368,601 A | 11/1994 | Sauer et al. | |
| 5,383,896 A | 1/1995 | Gershony et al. | |
| 5,383,897 A | 1/1995 | Wholey | |
| 5,383,899 A | 1/1995 | Hammerslag | |
| RE34,866 E | 2/1995 | Kensey et al. | 606/213 |
| 5,391,183 A | 2/1995 | Janzen et al. | |
| 5,392,918 A | 2/1995 | Harrison | |
| 5,397,331 A * | 3/1995 | Himpens et al. | 606/151 |
| 5,403,328 A | 4/1995 | Shallman | |
| 5,403,329 A | 4/1995 | Hinchcliffe | |
| 5,405,354 A | 4/1995 | Sarrett | |
| 5,411,520 A | 5/1995 | Nash et al. | |
| 5,417,699 A | 5/1995 | Klein et al. | |
| 5,431,639 A | 7/1995 | Shaw | |
| 5,431,666 A | 7/1995 | Sauer et al. | |
| 5,437,631 A | 8/1995 | Janzen | |
| 5,441,517 A | 8/1995 | Kensey et al. | |

(Continued)

*Primary Examiner*—Julian W Woo
(74) *Attorney, Agent, or Firm*—Holland & Hart

(57) ABSTRACT

An internal tissue puncture closure method and apparatus. The method and apparatus provide a folded sealing plug that provides more surface area than conventional plugs to more fully cover and seal an external situs of an internal tissue puncture. The folded sealing plug may have a weave pattern that tends to cause the sealing plug to corkscrew into the internal tissue puncture as it is compressed toward an anchor placed inside of the tissue puncture.

39 Claims, 6 Drawing Sheets

U.S. PATENT DOCUMENTS

| | | |
|---|---|---|
| 5,443,481 A | 8/1995 | Lee |
| 5,462,561 A | 10/1995 | Voda |
| 5,486,195 A | 1/1996 | Myers et al. |
| 5,496,332 A | 3/1996 | Sierra et al. |
| 5,496,335 A | 3/1996 | Thomason et al. |
| 5,507,744 A | 4/1996 | Tay et al. |
| 5,507,758 A | 4/1996 | Thomason et al. |
| 5,527,322 A | 6/1996 | Klein et al. |
| 5,531,759 A | 7/1996 | Kensey et al. ............... 606/213 |
| 5,545,178 A * | 8/1996 | Kensey et al. ............... 606/213 |
| 5,549,633 A | 8/1996 | Evans et al. |
| 5,571,181 A | 11/1996 | Li |
| 5,591,205 A | 1/1997 | Fowler |
| 5,593,422 A | 1/1997 | Muijs Van De Moer et al. |
| 5,601,603 A | 2/1997 | Illi |
| 5,613,974 A | 3/1997 | Andreas et al. |
| 5,620,461 A | 4/1997 | Muijs Van de Moer et al. |
| 5,626,601 A | 5/1997 | Gershony et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,653,730 A | 8/1997 | Hammerslag |
| 5,662,681 A * | 9/1997 | Nash et al. .................. 606/213 |
| 5,665,106 A | 9/1997 | Hammerslag |
| 5,674,231 A | 10/1997 | Green et al. |
| 5,676,689 A | 10/1997 | Kensey et al. |
| 5,681,334 A | 10/1997 | Evans et al. |
| 5,700,277 A | 12/1997 | Nash et al. |
| 5,707,393 A | 1/1998 | Kensey et al. |
| 5,716,413 A * | 2/1998 | Walter et al. ................ 424/423 |
| 5,720,765 A * | 2/1998 | Thal .......................... 606/232 |
| 5,725,498 A | 3/1998 | Janzen et al. |
| 5,725,551 A | 3/1998 | Myers et al. |
| 5,728,114 A | 3/1998 | Evans et al. ................. 606/148 |
| 5,728,122 A | 3/1998 | Leschinsky et al. |
| 5,728,132 A | 3/1998 | Van Tassel et al. |
| 5,728,133 A | 3/1998 | Kontos |
| 5,728,134 A | 3/1998 | Barak |
| 5,741,223 A | 4/1998 | Janzen et al. |
| 5,746,755 A | 5/1998 | Wood et al. |
| 5,755,727 A | 5/1998 | Kontos |
| 5,759,194 A | 6/1998 | Hammerslag |
| 5,766,183 A | 6/1998 | Sauer |
| 5,766,206 A | 6/1998 | Wijkamp et al. |
| 5,782,861 A | 7/1998 | Cragg et al. |
| 5,792,154 A * | 8/1998 | Doan et al. .................. 606/151 |
| 5,792,173 A | 8/1998 | Breen et al. |
| 5,810,810 A | 9/1998 | Tay et al. |
| 5,810,846 A | 9/1998 | Virnich et al. |
| 5,810,884 A | 9/1998 | Kim |
| 5,814,065 A | 9/1998 | Diaz |
| 5,820,631 A | 10/1998 | Nobles |
| 5,827,299 A | 10/1998 | Thomason et al. |
| 5,830,130 A | 11/1998 | Janzen et al. |
| 5,843,124 A | 12/1998 | Hammerslag |
| 5,853,421 A | 12/1998 | Leschinsky et al. |
| 5,855,585 A | 1/1999 | Kontos |
| 5,860,990 A | 1/1999 | Nobles et al. |
| 5,861,004 A | 1/1999 | Kensey et al. |
| 5,861,005 A | 1/1999 | Kontos |
| 5,868,762 A | 2/1999 | Cragg et al. |
| 5,876,411 A | 3/1999 | Kontos |
| 5,902,311 A | 5/1999 | Andreas et al. |
| 5,906,631 A | 5/1999 | Imran ........................ 606/213 |
| 5,910,155 A | 6/1999 | Ratcliff et al. |
| 5,916,236 A | 6/1999 | Muijs Van de Moer et al. |
| 5,919,207 A | 7/1999 | Taheri |
| 5,935,147 A | 8/1999 | Kensey et al. ............... 606/213 |
| 5,941,897 A | 8/1999 | Myers |
| 5,948,425 A | 9/1999 | Janzen et al. ............... 424/422 |
| 5,957,952 A | 9/1999 | Gershony et al. |
| 5,964,782 A | 10/1999 | Lafontaine et al. |
| 5,976,161 A | 11/1999 | Kirsch et al. |
| 5,980,539 A | 11/1999 | Kontos |
| 5,997,555 A | 12/1999 | Kontos |
| 6,007,562 A | 12/1999 | Harren et al. |
| 6,007,563 A | 12/1999 | Nash et al. |
| 6,017,359 A | 1/2000 | Gershony et al. |
| 6,024,747 A | 2/2000 | Kontos |
| 6,027,523 A * | 2/2000 | Schmieding ................ 606/232 |
| 6,033,401 A | 3/2000 | Edwards et al. |
| 6,033,427 A | 3/2000 | Lee |
| 6,036,721 A | 3/2000 | Harren et al. |
| 6,042,601 A | 3/2000 | Smith |
| 6,045,569 A | 4/2000 | Kensey et al. |
| 6,048,357 A | 4/2000 | Kontos |
| 6,048,358 A | 4/2000 | Barak |
| 6,063,085 A | 5/2000 | Tay et al. |
| 6,071,300 A | 6/2000 | Brenneman et al. |
| 6,077,279 A | 6/2000 | Kontos |
| 6,090,130 A | 7/2000 | Nash et al. |
| 6,110,184 A | 8/2000 | Weadock |
| 6,120,524 A | 9/2000 | Taheri |
| 6,126,675 A | 10/2000 | Shchervinsky et al. |
| 6,136,010 A | 10/2000 | Modesitt et al. |
| 6,139,556 A | 10/2000 | Kontos |
| 6,162,192 A | 12/2000 | Cragg ........................ 604/15 |
| 6,174,322 B1 | 1/2001 | Schneidt |
| 6,179,863 B1 | 1/2001 | Kensey et al. |
| 6,183,496 B1 | 2/2001 | Urbanski |
| 6,197,042 B1 | 3/2001 | Ginn et al. |
| 6,206,895 B1 | 3/2001 | Levinson |
| 6,231,561 B1 | 5/2001 | Frazier et al. |
| 6,245,080 B1 | 6/2001 | Levinson |
| 6,398,796 B2 | 6/2002 | Levinson |
| 6,425,911 B1 | 7/2002 | Akerfeldt et al. |
| 6,425,924 B1 * | 7/2002 | Rousseau .................... 606/151 |
| 6,508,828 B1 * | 1/2003 | Akerfeldt et al. ............ 606/215 |
| 6,547,806 B1 | 4/2003 | Ding |
| 6,569,185 B2 | 5/2003 | Ungs |
| 6,596,012 B2 | 7/2003 | Akerfeldt et al. |
| 6,596,014 B2 | 7/2003 | Levinson et al. |
| 6,652,560 B1 * | 11/2003 | Gerke et al. ................. 606/232 |
| 6,682,489 B2 | 1/2004 | Tenerz et al. |
| 6,712,837 B2 | 3/2004 | Akerfeldt et al. |
| 6,860,895 B1 | 3/2005 | Akerfeldt et al. |

* cited by examiner

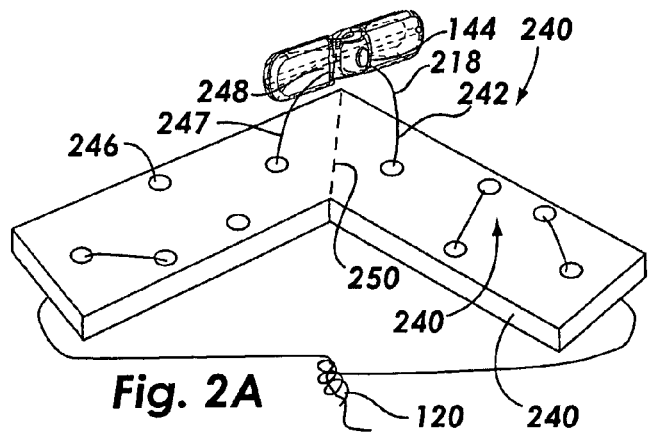
Fig. 2A
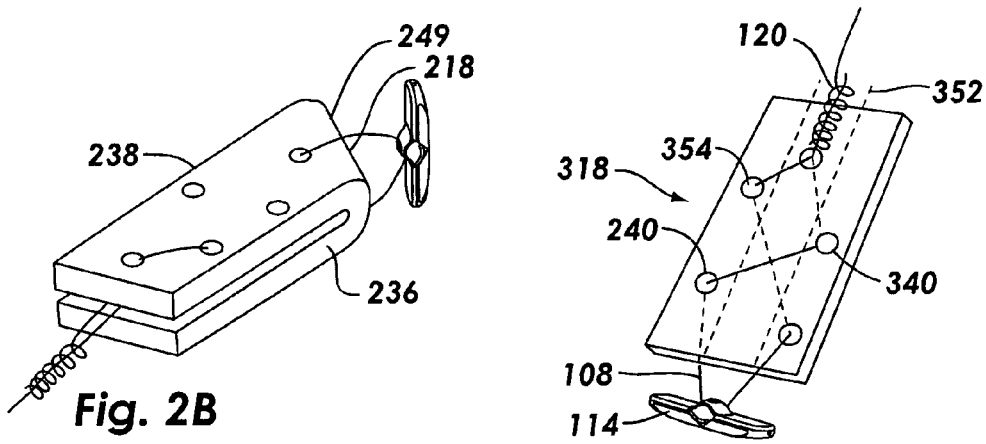
Fig. 2B
Fig. 3A
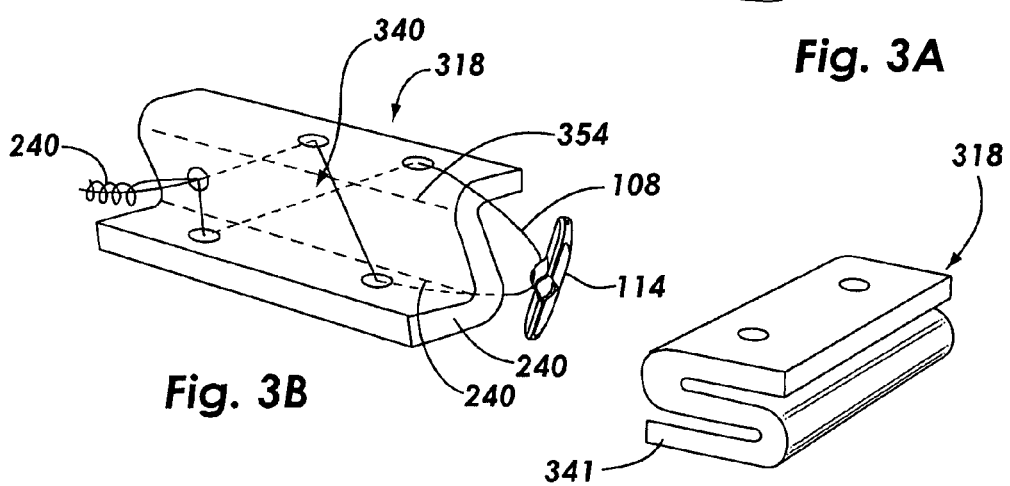
Fig. 3B
Fig. 3C

VASCULAR SEALING DEVICE WITH HIGH SURFACE AREA SEALING PLUG

FIELD OF THE INVENTION

The present invention relates to medical devices, and, more particularly, to an internal tissue puncture closure apparatus.

BACKGROUND OF THE INVENTION

Various medical procedures, particularly cardiology procedures, involve accessing a corporeal vessel or other lumen through a percutaneous sheath. Access to the vessel necessarily requires the formation of a hole or puncture in the vessel wall so that a medical procedure can be performed. After the particular medical procedure has been performed, the sheath and other tools must eventually be removed from the vessel and the access hole in the vessel wall must be closed.

Therefore, a number of closure devices have been developed to close the hole in the vessel wall. Examples of prior vascular puncture closure devices are described in U.S. Pat. Nos. 6,179,863; 6,090,130; and 6,045,569 and related patents that are hereby incorporated by reference. The closure devices disclosed in the above-referenced patents and others are intended to seal an arteriotomy with an absorbable anchor and a collagen sponge. The anchor and the collagen sponge are held together with a self-tightening slip knot at the arteriotomy by a length of absorbable suture. The anchor and collagen sponge are cinched together across the arteriotomy, creating a sandwich-like effect. In order to seal the hole, it is necessary to apply a compressive sealing force to the arteriotomy, which is normally supplied by the slip-knotted suture. However, if the collagen sponge does not position correctly over the hole, there is potential for bleeding. The prior designs for the collagen sponge are generally rectangular, and have a three-hole or five-hole weave pattern allowing the collagen sponge to corkscrew through the puncture tract as the suture is pulled. However, the size of the rectangular-shaped collagen sponge is limited, because the collagen sponge must fit inside a carrier tube of the tissue puncture closure device.

Because of the limited size and surface area available for the standard rectangular-shaped collagen sponge, sometimes the hole in the vessel is not completely covered or adequately sealed. If the hole is not adequately sealed, residual bleeding may occur, resulting in an extended period of time to reach hemostasis. Therefore, there is a need to provide better coverage at a tissue puncture site to cover a wider area at arterial or other punctures.

SUMMARY OF THE INVENTION

In one of many possible embodiments, the present invention provides a tissue puncture closure device for partial insertion into and sealing of an internal tissue wall puncture. The tissue puncture closure device comprises a filament, an anchor for insertion through the tissue wall puncture attached to the filament at a first end of the closure device, and a sealing plug disposed proximal of the anchor. The sealing plug, however, includes a high surface area for providing more coverage at the tissue wall puncture site. The high surface area is provided by folding the sealing plug in various configurations, such as an S-fold, a V-fold, two engaged U-folds, or other folds. In addition, other sealing plug configurations such as a cross or X-shaped collagen sponge may provide higher surface areas.

The foregoing and other features, utilities and advantages of the invention will be apparent from the following description of preferred embodiments of the invention as illustrated in the accompanying drawings.

BRIEF DESCRIPTION OF THE DRAWING

The accompanying drawings illustrate various embodiments of the present invention and are a part of the specification. The illustrated embodiments are merely examples of the present invention and do not limit the scope of the invention.

FIG. 2A is a perspective view of a sealing plug and anchor for use with the tissue puncture closure device of FIG. 1A. The sealing plug is shown in an open or unfolded position according to one embodiment of the present invention.

FIG. 2B is a perspective end view of the sealing plug shown in FIG. 2A, with the sealing plug folded to a closed position according to one embodiment of the present invention.

FIG. 3A is a perspective view of another sealing plug and anchor for use with the tissue puncture closure device of FIG. 1A. The sealing plug is shown in an open or unfolded position according to one embodiment of the present invention.

FIG. 3B is a perspective view of the sealing plug shown in FIG. 3A, with the sealing plug partially folded according to one embodiment of the present invention.

FIG. 3C is a perspective end view of the sealing plug shown in FIG. 3B, with the sealing plug fully folded according to one embodiment of the present invention.

DETAILED DESCRIPTION

The present specification describes techniques and apparatus for closing an internal tissue wall puncture, preferably using a closure device and an insertion sheath, while reducing the likelihood of leaks. The reduction in the likelihood of leaks is facilitated according to some embodiments by providing more sealing material or more sealing material surface area to provide better coverage at the tissue wall puncture. While the methods and devices shown and described below include reference to specific insertion sheaths and puncture sealing devices, the application of principles described herein to close a tissue puncture is not limited to these specific devices. The principles described herein may be used to close or seal any interior tissue puncture, particularly punctures or incisions in arteries or other bodily lumens. Therefore, while the description below is directed primarily to arterial procedures, the methods and apparatus may be used according to principles described herein with any lumen to control bleeding.

As used in this specification and the appended claims, the term "tissue" means an aggregation of morphologically similar cells and associated intercellular matter acting together to perform one or more specific functions in a body. A "lumen" is any open space or cavity in a bodily organ, especially in a blood vessel. "Open," when used as an adjective to modify a shape means without any folds or modifications. "Surface area" refers to areas of exposed and unexposed surfaces, including folded surfaces that may be initially internal due to folding. "Latitude" refers to a sidewise distance from a given point or line; a breadth or width. Therefore, "latitudinally" is used as an adverb with reference to a fold across a width, as opposed to a length, of an item. The words "including" and "having," as used in the specification, including the claims, have the same meaning as the word "comprising."

Figure 1A:
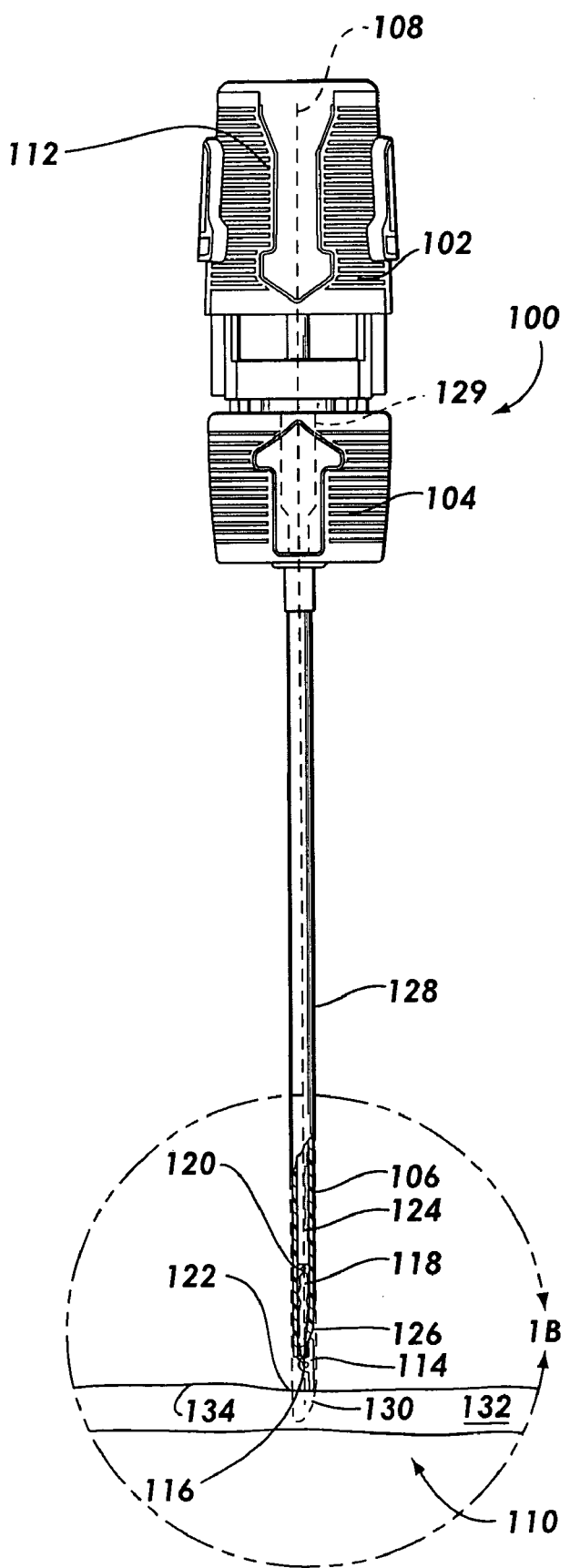
FIG. 1A is a cutaway assembly view of an internal tissue puncture closure device and an insertion sheath according to one embodiment of the present invention.
Figure 1B:
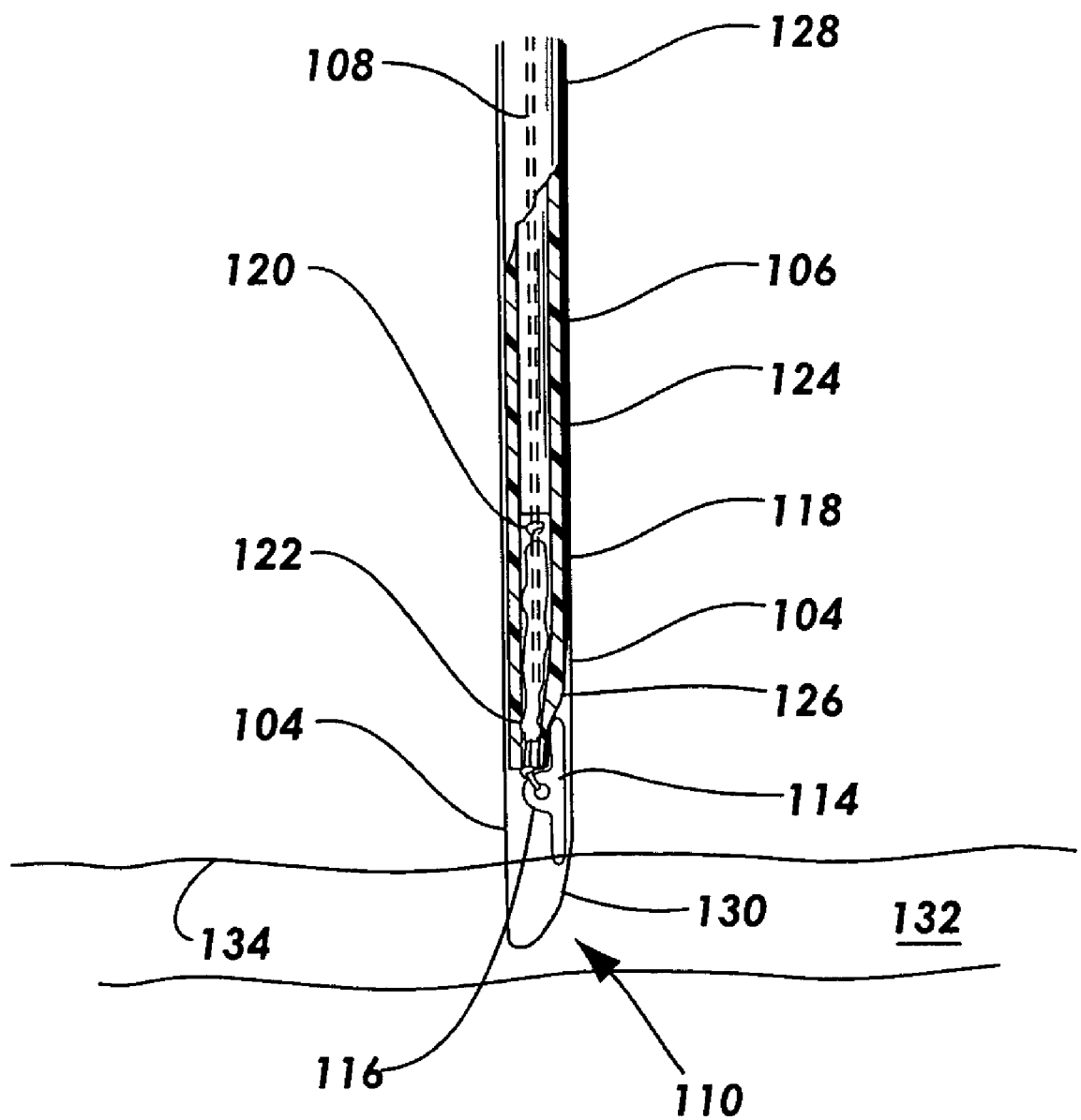
FIG. 1B is a detail of the cutaway section of FIG. 1A.

Referring now to the drawings, and in particular to FIGS. 1A-1B, an internal tissue puncture closure assembly 100 including a tissue puncture closure device 102 inserted through an insertion sheath 104 is shown according to one embodiment of the present invention. The tissue puncture closure device 102 includes a carrier tube 106 with a filament such as a suture 108 extending at least partially therethrough. According to FIGS. 1A-1B, the suture 108 extends from a first or distal end 110 of the closure device 102 to a second or proximal end 112 of the closure device 102. External to the first or distal end 110 of the carrier tube 106 is an internal component, which according the present embodiment is an anchor 114. The anchor 114 is an elongated, stiff, low-profile member with a protruding eye 116. The anchor 114 is made of a non-hemostatic biologically resorbable polymer according to the embodiment shown.

The suture 108 is also made of a biologically resorbable material and is threaded through the anchor 114. An external component, which, according to the present embodiment, is a biologically resorbable collagen sponge 118 that acts as a sealing plug, is initially disposed within the carrier tube 106 proximal of the anchor 114. The suture 108 weaves through the collagen sponge 118 and ties into a self-tightening knot 120 proximal of the collagen sponge 118. Following deployment of anchor and the collagen sponge 118, the suture 108 may be pulled to compress or sandwich the anchor 114 and the collagen sponge 118 across an interior tissue puncture in a bodily lumen, such as an arteriotomy 122.

The tissue puncture closure device 102 may also include a tamping tube 124 disposed within the carrier tube 106 proximal to the collagen sponge 118. The tamping tube 124, if used, is slidingly mounted over the suture 108. The tamping tube 124 may be used to tamp the collagen sponge 118 toward the arteriotomy 122.

At the distal end 110 of the carrier tube 106 is a nest 126. Prior to deployment of the anchor 114 within an artery, the protruding eye 116 seats outside the distal end 110 of the carrier tube 106, and one wing of the anchor 108 rests in the nest 126. The nest 126 is typically crushed into the carrier tube 102 to a sufficient depth such that the anchor 114 is flush with an outer diameter of the carrier tube 106.

The flush arrangement of the anchor 114 and carrier tube 106 allows the anchor 114 to be inserted into the insertion sheath 104, and eventually through an internal tissue puncture such as the arteriotomy 122. The insertion sheath 104 comprises a generally flexible tubular member 128 with a hemostatic valve 129 at a proximal end thereof. The insertion sheath 104 includes a fold 130 disposed at a distal end. The fold 130 acts as a one-way valve to the anchor 114. The fold 130 is a plastic deformation in a portion of the tubular member 128 that elastically flexes as the anchor 114 is pushed out through the distal end of the tubular member 128. However, as the anchor 114 passes though and out of the distal end of the tubular member 128, the fold 130 attempts to spring back to its original deformed position such that the fold 130 engages the carrier tube 106.

After the anchor 114 passes through the distal end 130 of the tubular member 128, the anchor 114 enters the arteriotomy 122 in an artery 132 or other lumen through a percutaneous incision in a patient. When the anchor 114 enters the artery 132, it rotates and deploys such that its wings are arranged adjacent to an internal wall 134 of the artery 132. The puncture closure device 102 may be pulled in a proximal direction with respect to the insertion sheath 104 to facilitate rotation of the anchor 114. The fold 130 in the insertion sheath 104 prevents reinsertion of the anchor 114 into the insertion sheath 104 and causes the anchor 114 to rotate if it does not do so automatically after passing out of the insertion sheath 104.

When the anchor 114 is properly positioned inside the artery 132 abutting the internal wall 134, the closure device 102 and the insertion sheath 104 are withdrawn from the arteriotomy 122 together. However, because the anchor 114 is established inside the artery 132, retraction of the insertion sheath 104 and the closure device 102 exposes the collagen sponge 118 and, if used, the tamping tube 124. Accordingly, the collagen sponge 118 is deposited at an external situs of the arteriotomy 122 opposite of the anchor 114.

However, depositing the collagen sponge 114 without compressive force at the puncture arteriotomy 122 does not normally seal the hole. Therefore, according to one embodiment of the present invention, an operator may apply tension to the suture 108 to compress the collagen sponge 118 and the anchor 114 across the arteriotomy 122. The suture 108 weaves distally though the collagen sponge 118 and the anchor 114, then returns proximally back through the collagen sponge 118 where it is tied into the self-tightening knot 120 that cinches the collagen sponge 118 toward the anchor 114 as tension is applied to the suture.

The collagen sponge 118 or other sealing plug may comprise a number of shapes to provide better coverage and therefore more reliable sealing of the arteriotomy 122 than previously available. Various embodiments of sealing plugs are shown and described in more detail below with reference to FIGS. 2A-6B. The configurations of the sealing plugs shown in the figures and described below may comprise the collagen sponge 118 of the internal tissue puncture closure assembly 100 shown in FIGS. 1A-1B or other devices.

The sealing plugs according to some embodiments of the present invention comprise shapes having a higher surface-area-to-volume-ratio than an open rectangle for a given set of rectangular dimensions. For example, an open rectangle fitting into dimensions measuring 4 units long, 2 units wide, and 1 unit thick has a surface area of 28 units$^2$, a volume of 8 units$^3$, and therefore a surface-area-to-volume-ratio of 28:8 or 3.5:1. However, referring to FIGS. 2A-2B, a sealing plug 218 in relation to the anchor 114 is shown according to one embodiment that has a greater surface-area-to-volume-ratio than 3.5:1 for the same rectangular dimensions. The surface area of the sealing plug 218, if sized to fit within the same 4×2×1 unit dimensions and folded as shown in FIG. 2B has an approximate surface area of 42 units$^2$, a volume of 8 units$^3$, and therefore a surface-area-to-volume-ratio of 42:8 or 5.25:1.

The sealing plug 218 is shown in FIG. 2A in an open or unfolded position as it appears after being deployed from the carrier tube 106 (FIG. 1A). According to FIG. 2A, the sealing plug 218 is arranged in a generally V-shape with a first portion or leg 236 and a second portion or leg 238 defining the V-shape. The first leg 236 includes a first filament weave pattern 240 comprising a plurality of holes. A first portion 242 of the filament 108 extends from a first side 244 of the anchor 114 and loops through the first filament weave pattern 240. Similarly, the second leg 238 includes a second filament weave pattern 246 comprising a plurality of holes. The first and second weave patterns 240, 246 shown each comprise a five-hole zigzagging pattern, but this is not necessarily so. There may be other weave patterns with any number of holes, and while the first and second weave patterns 240, 246 are shown identically, they are not necessarily always the same. A second portion 247 of the filament 108 extends from a second side 248 of the anchor 114 and loops through the second weave pattern 246. The first and second portions 242, 247 of the filament 108 are then tied into the self-tightening knot 120 shown. Therefore, the anchor 114 is arranged substantially in the middle of sealing plug 218, as opposed to being attached at an end, which is typical of the prior art.

The first and second legs 236, 238 of sealing plug 218 meet at a latitudinal vertex or centerline 250. To facilitate insertion of the sealing plug 218 into the carrier tube 106 (FIG. 1A), the sealing plug 218 is folded at the centerline 250 into a generally rectangular configuration shown in FIG. 2B with the two legs 236, 238 substantially aligned, with one surface 251 sloped along the centerline 250 after the fold.

Referring next to FIGS. 3A-3C, another embodiment of a sealing plug 318 is shown according to the present invention. As shown in FIG. 3A, the sealing plug 318 may initially comprise a generally rectangular shape. However, the generally rectangular shape is substantially wider than a conventional sealing plug. The sealing plug 318 according to FIG. 3A is two-to-three times wider than a conventional sealing plug or more. While the wider sealing plug 318 provides more surface area and coverage to the arteriotomy 122, it does not fit into the carrier tube 106 (FIG. 1A) in the configuration shown. Therefore, the sealing plug 318 is tri-folded as shown in FIG. 3B. The sealing plug 318 is longitudinally folded at least twice along two longitudinal axes 352, 354 to form a generally S-shape or trifold, shown from an end view in FIG. 3C. By folding the sealing plug 318 at least twice as shown, the sealing plug 318 fits into the carrier tube 106 (FIG. 1A) and also provides better sealing coverage when deployed.

Similar to the embodiment of FIGS. 2A-2B, the sealing plug 318 of FIGS. 3A-3C includes a weave pattern 340. The filament 108 extends though the weave pattern 340, loops through the anchor 114, returns back to the through the weave pattern, and then ties into the self-tightening knot 120 proximal of the sealing plug 318. However, unlike the embodiment shown in FIGS. 2A-2B, the anchor 114 is attached at an end 341 of the sealing plug 318 according to FIGS. 3A-3C. The weave pattern 340 is a spiral configuration and tends to cause the sealing plug 318 to "corkscrew" toward the anchor and seal the arteriotomy 122 (FIG. 1A) when the filament 108 is put into tension.

Figure 4A:
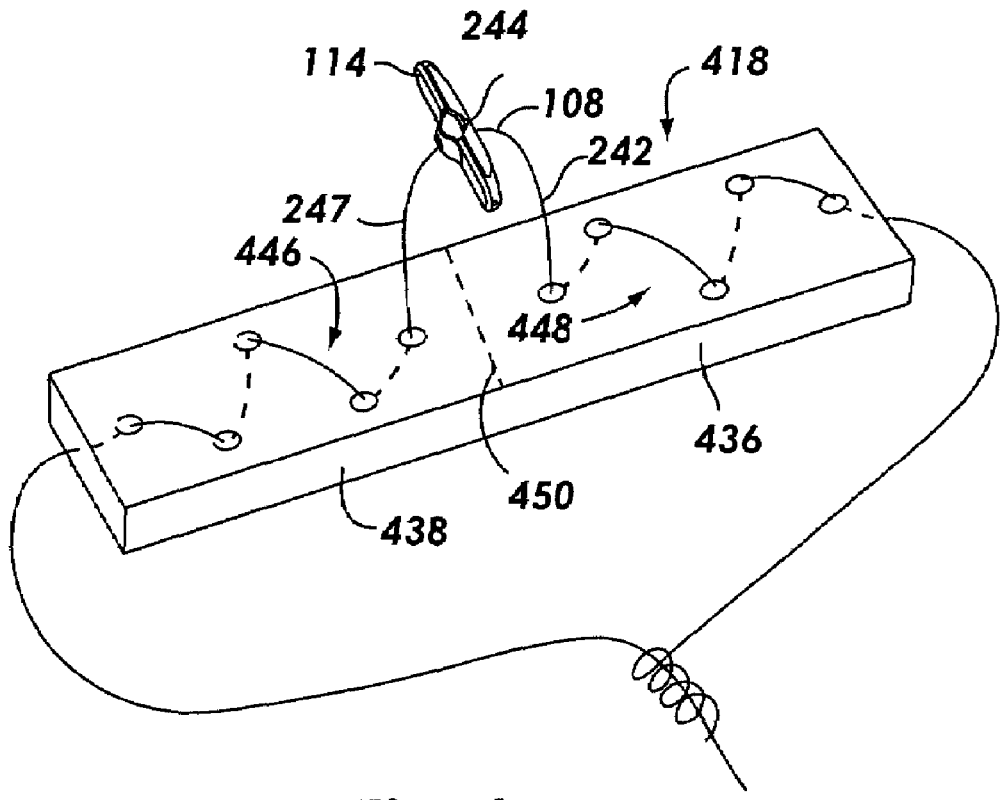
FIG. 4A is a perspective view of an elongated sealing plug and anchor for use with the tissue puncture closure device of FIG. 1A. The elongated sealing plug is shown in an open or unfolded position according to one embodiment of the present invention.
Figure 4B:
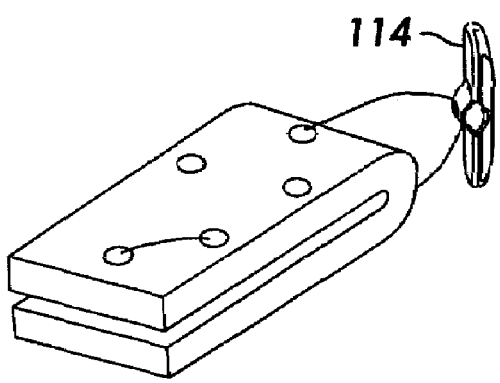
FIG. 4B is a perspective end view of the sealing plug shown in FIG. 4A, with the sealing plug folded to a closed position according to one embodiment of the present invention.

Referring next to FIGS. 4A-4B, a sealing plug 418 according to another embodiment of the present invention shown. The sealing plug 418 of FIGS. 4A-4B is similar to the embodiment shown in FIGS. 2A-2B, however the sealing plug 418 is arranged in a rectangular manner when it is both folded and unfolded. The sealing plug 418 includes a first half 436 with a first weave pattern 440, and a second half 438 with a second weave pattern 446. As with the embodiment of FIGS. 2A-2B, the first portion 242 of the filament 108 extends from the first side 244 of the anchor 114 and loops through the first filament weave pattern 440. The second portion 247 of the filament 108 loops through the second filament weave pattern 446. Therefore, again the anchor 114 is arranged substantially in the middle of sealing plug 418, as opposed to an attachment at an end.

The first and second halves 436, 438 of the sealing plug 418 meet at a latitudinal centerline 450. To facilitate insertion of the sealing plug 418 into the carrier tube 106 (FIG. 1A), the sealing plug 418 is folded at the centerline 450 into the configuration shown in FIG. 4B with the two halves 436, 438 facing one another.

Figure 5A:
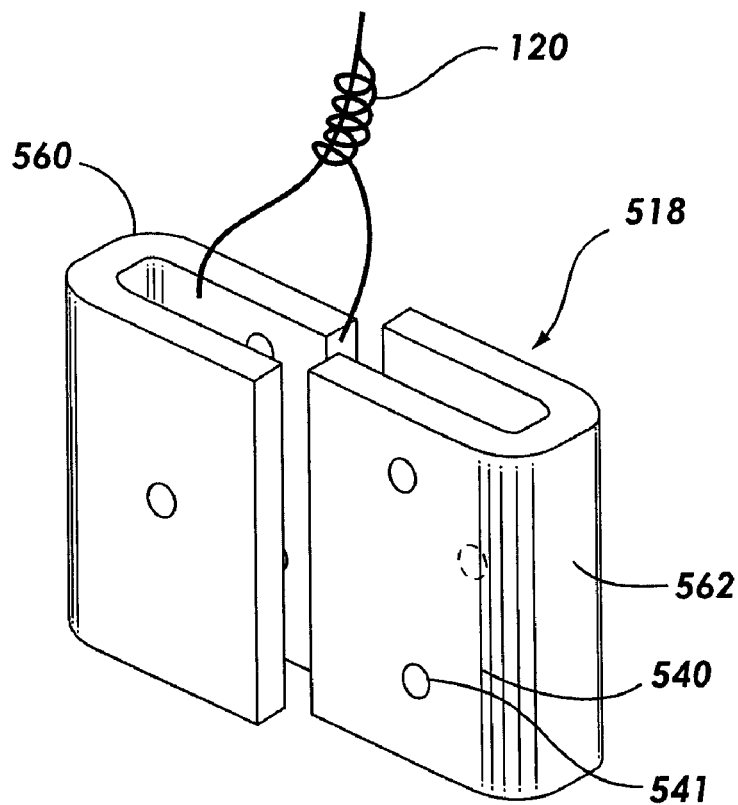
FIG. 5A is a perspective side view of another sealing plug and anchor for use with the tissue puncture closure device of FIG. 1A according to one embodiment of the present invention.
Figure 5B:
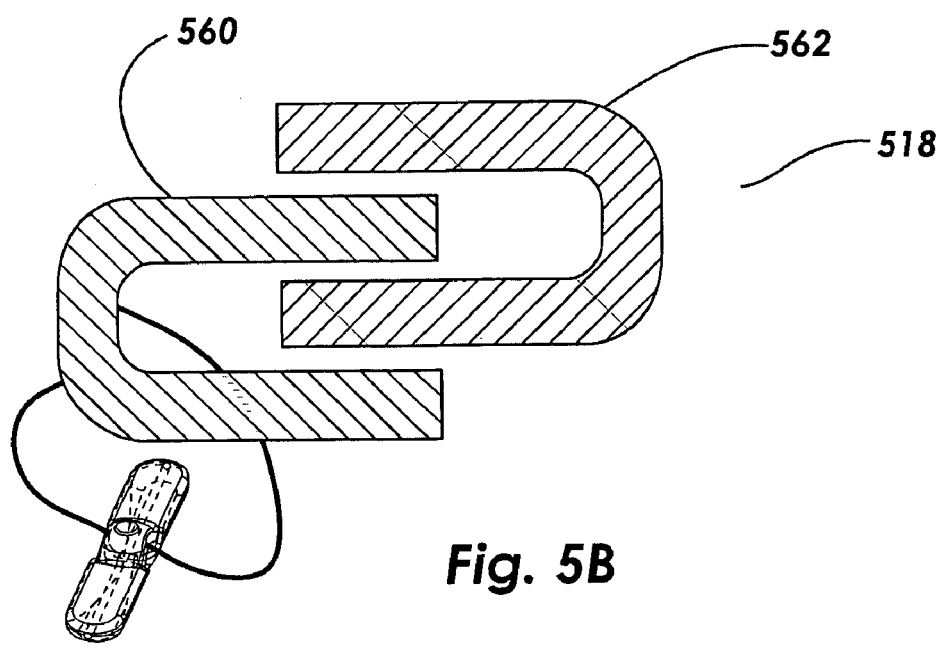
FIG. 5B is a perspective end view of the sealing plug shown in FIG. 5A according to one embodiment of the present invention.

Referring next to FIGS. 5A-5B, another folded configuration of a sealing plug 518 is shown. The sealing plug 518 of FIGS. 5A-5B comprises two separate components, a first component 560 and a second component 562. According to FIG. 5A, the two components 560, 562 are generally rectangular and similar or identical to one another. Each of the two components 560, 562 is longitudinally folded into a general U-shape and engaged or interconnected with the other as illustrated more clearly in FIG. 5B. The folding and engagement facilitates insertion of the sealing plug 518 into the carrier tube 106 (FIG. 1A).

The anchor 114 is attached via the suture 108 at a longitudinal end 541, as opposed to a middle, of the sealing plug 518. The suture 108 passes distally through a portion of a weave pattern 540 in the sealing plug 518, loops through the anchor 114, and returns proximally to pass through another portion of the weave pattern 540. As with the other embodiments, the filament 108 is tied into a self-tightening slip knot 120 proximal of the sealing plug.

Figures 6A, 6B:
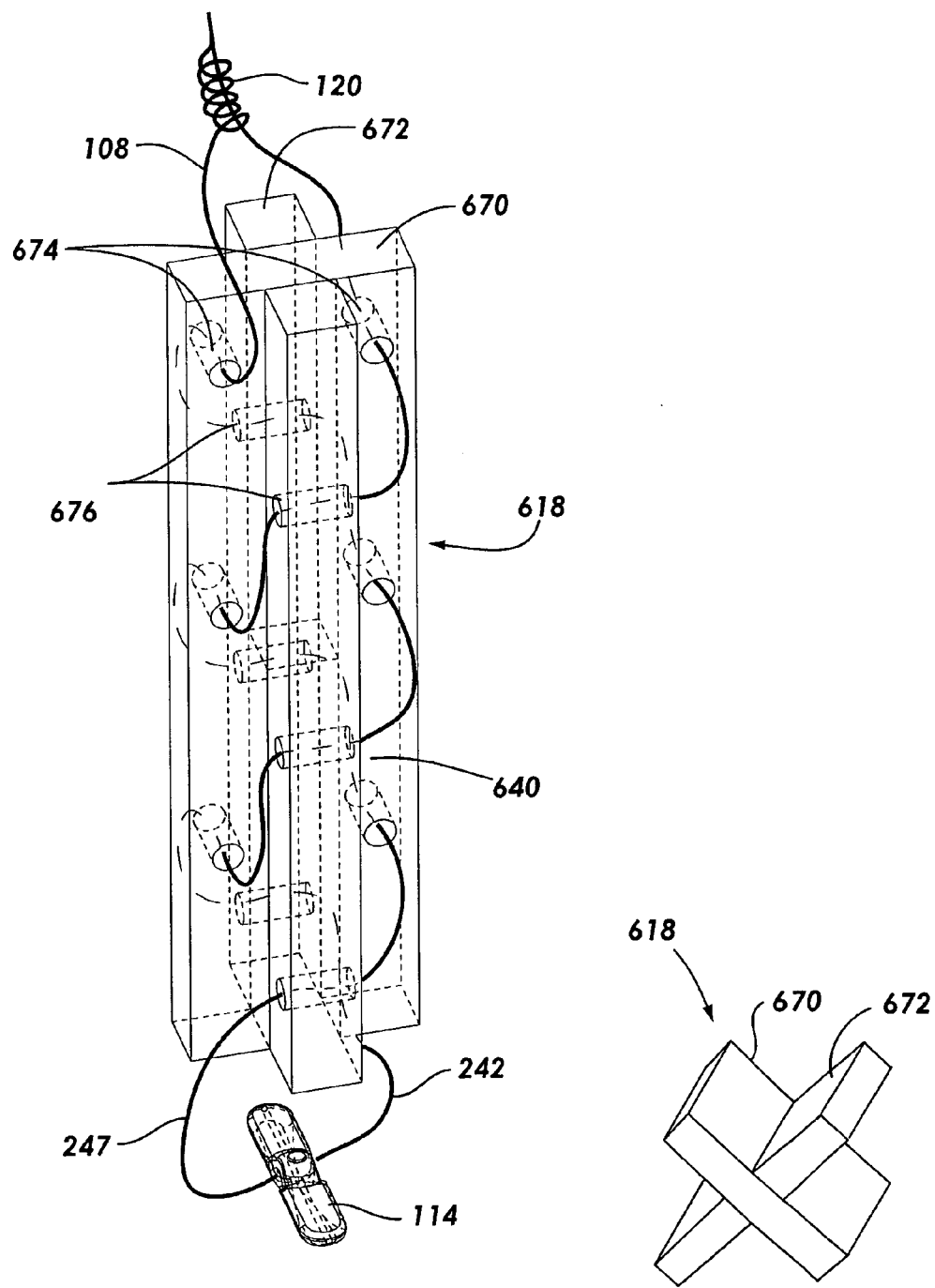
FIG. 6A is a perspective side view of another sealing plug configuration and anchor for use with the tissue puncture closure device of FIG. 1A according to one embodiment of the present invention.
FIG. 6B is a perspective end view of the sealing plug shown in FIG. 6A according to one embodiment of the present invention Throughout the drawings, identical reference numbers designate similar, but not necessarily identical, elements.

While the embodiment shown and described above disclose various ways to fold a sealing plug to provide more surface area and better coverage than conventional collagen sponges used in tissue puncture closure devices, other embodiments that do not include folds may also provide similar advantages. For example, another sealing plug 618 is illustrated in FIGS. 6A-6B according to principles of the present invention. The sealing plug 618 of FIGS. 6A-6B comprises two walls or cross members 670, 672 having a weave pattern 640 through with the filament 108 extends. The two cross members 670, 672 are arranged in a generally X-shaped configuration in cross-section. According to some embodiments, the two cross members 670, 672 are substantially perpendicular to one another, although this in not necessarily so. Angles other than right angles may also be used between the two cross members 670, 672 or others.

The weave pattern 640 through the two cross members 670, 672 comprises a plurality of holes alternating between the first and second cross members 670, 672. The holes are staggered longitudinally such that the first portion 242 of the filament 108 may alternately extend through a first set of holes in the first and second cross members 670, 672 in a spiral pattern, and the second portion 247 may alternately extend through a second set of holes in the first and second cross members 670, 672 in a complementary spiral pattern. According to FIGS. 6A-6B, the weave pattern is comprised of a first set of equally longitudinally spaced hole pairs 674 in the first cross member 670, and a second set of equally longitudinally spaced hole pairs 676 in the second cross member 672 staggered from the first set 674. The weave pattern 640 thus provides the "corkscrew" effect as the filament 108 is put in tension, and results in compression between the anchor 114 and the sealing plug 618. The cross member configuration for a sealing plug provides more surface area to more effectively seal internal tissue punctures. And while only two cross members 670, 672 are shown in FIGS. 6A-6B, more cross members may also be added according to principles described herein.

While the invention has been particularly shown and described with reference to embodiments thereof, it will be understood by those skilled in the art that various other changes in the form and details may be made without departing from the scope of the invention.

What is claimed is:

1. A tissue puncture closure device for partial insertion into and sealing of an internal tissue wall puncture, comprising:
   a carrier tube;
   a filament;
   an anchor configured to be inserted through the tissue puncture, the anchor being attached to the filament at a first end of the closure device;
   a sealing plug positioned in the carrier tube, the sealing plug comprising:
      a first plurality of holes including one hole in the sealing plug, the first plurality of holes forming a first weave pattern in a first portion of the sealing plug, wherein a first portion of the filament extends from a first side of the anchor and passes through the first plurality of holes;
      a second plurality of holes including another hole in the sealing plug, the second plurality of holes forming a second weave pattern in a second portion of the sealing plug, wherein a second portion of the filament extends from a second side of the anchor and passes through the second plurality of holes;
   wherein the filament passes through the one hole in the sealing plug to a hole in the anchor and back through the another hole in the sealing plug;
   wherein the one hole in the sealing plug is the last hole in the sealing plug that the filament passes through before entering the hole in the anchor and the another hole in the sealing plug is the first hole in the sealing plug that the filament passes through after exiting the hole in the anchor; and
   wherein the filament passes through at least four holes in the sealing plug.

2. A tissue puncture closure device for partial insertion into and sealing of an internal tissue wall puncture according to claim 1 wherein the sealing plug is folded at least twice.

3. A tissue puncture closure device for partial insertion into and sealing of an internal tissue wall puncture according to claim 2 wherein the sealing plug is shaped at least approximately like an S.

4. A tissue puncture closure device for partial insertion into and sealing of an internal tissue wall puncture according to claim 1 wherein the sealing plug is folded.

5. A tissue puncture closure device for partial insertion into and sealing of an internal tissue wall puncture according to claim 4 wherein the sealing plug is folded between the one hole in the sealing plug and the another hole in the sealing plug.

6. A tissue puncture closure device for partial insertion into and sealing of an internal tissue wall puncture according to claim 1 wherein the first weave pattern and the second weave pattern each comprise a five-hole zigzag arrangement.

7. A tissue puncture closure device for partial insertion into and sealing of an internal tissue wall puncture according to claim 1 wherein the sealing plug and filament each comprise biologically resorbable materials.

8. A tissue puncture closure device for partial insertion into and sealing of an internal tissue wall puncture according to claim 1 wherein the sealing plug is folded between the first weave pattern and the second weave pattern.

9. A tissue puncture closure device for partial insertion into and sealing of an internal tissue wall puncture according to claim 1 wherein the sealing plug shape comprises an X-shape in cross-section.

10. A tissue puncture closure device for partial insertion into and sealing of an internal tissue wall puncture according to claim 9, further comprising a plurality of holes including the one hole in the sealing plug and the another hole in the sealing plug, the plurality of holes forming a staggered weave pattern in the sealing plug.

11. A tissue puncture closure device for partial insertion into and sealing of an internal tissue wall puncture according to claim 9 wherein the filament alternately passes through generally perpendicular walls of the sealing plug.

12. A tissue puncture closure device for partial insertion into and sealing of an internal tissue wall puncture according to claim 11 wherein the plurality of holes includes a first set of equally longitudinally spaced hole pairs in one of the perpendicular walls and a second set of equally longitudinally spaced hole pairs in another one of the perpendicular walls, the second set of hole pairs being staggered from the first set of hole pairs longitudinally.

13. A tissue puncture closure device for partial insertion into and sealing of an internal tissue wall puncture according to claim 1 wherein the sealing plug shape comprises two components, and wherein the one hole in the sealing plug is in one of the two components and the another hole in the sealing plug is in the other one of the two components.

14. A tissue puncture sealing device, comprising:
   an internal component configured to be positioned against an internal wall of a bodily lumen, the internal component comprising a stiff member;
   an external component configured to be positioned external to the lumen, the external component being folded so that one portion of the external component is in contact with another portion of the external component, the external component comprising a sponge material;
   wherein the external component is operatively connected to the internal component by a filament configured to compress and hold the internal and external components together to prevent fluid from passing through a puncture in the bodily lumen;
   wherein the filament passes through one hole in the external component to a hole in the internal component and back through another hole in the external component, the external component being folded between the one hole in the external component and the another hole in the external component;
   wherein the filament only passes once through each one of the one hole and the another hole; and
   wherein the tissue puncture sealing device is in an undeployed configuration.

15. A tissue puncture sealing device according to claim 14 wherein the internal component is a stiff anchor and the external component is a collagen sponge.

16. A tissue puncture sealing device according to claim 15 wherein the collagen sponge is folded twice longitudinally.

17. A tissue puncture sealing device according to claim 16 wherein the collagen sponge is substantially S-shaped.

18. A tissue puncture sealing device according to claim 14 wherein the external component comprises a plurality of holes including the one hole in the external component and the another hole in the external component, wherein the plurality of holes form a weave pattern, and wherein the filament weaves through a first portion of the weave pattern, through the internal component, and back Through a second portion of the weave pattern.

19. A tissue puncture sealing device according to claim 18 wherein the external component is folded between the first portion of the weave pattern and the second portion of the weave pattern.

20. A tissue puncture sealing device according to claim 18 wherein the external component is folded latitudinally.

21. A tissue puncture sealing device according to claim 14 wherein the external component comprises two legs folded along a centerline such that the two legs are substantially aligned.

22. A tissue puncture sealing device according to claim 14, wherein the external component includes a first external component and a second external component, the second external component being folded and in contact with the first external component.

23. A tissue puncture sealing device according to claim 22 wherein the first and second external components are each folded into generally U-shapes.

24. An internal tissue puncture closure device, comprising:
an anchor for insertion through a tissue puncture;
a filament threaded through the anchor;
a flexible sealing plug aft ached to the anchor by the filament;
wherein the sealing plug comprises two cross members each of which includes a plurality of holes which extend therethrough;
wherein the filament extends through the plurality of holes in each of the two cross members;
wherein the filament alternately extends through the plurality of holes in the two cross members in a spiral pattern; and
wherein the tissue puncture sealing device is configured so that applying a tension force to the filament moves the anchor and the sealing plug together.

25. An internal tissue puncture closure device according to claim 24 wherein the two cross members are arranged in a generally X-shape.

26. An internal tissue puncture closure device according to claim 25 wherein each of two portions of the filament extending from the anchor in opposite directions traverse separate holes through the two cross members.

27. A tissue puncture sealing device, comprising:
a filament;
an anchor attached to the filament and configured to be inserted through a tissue wall puncture; and
a sealing plug disposed proximal of the anchor, the sealing plug including a first plurality of openings and a second plurality of openings;
wherein the filament passes through at least two openings from the first plurality of openings, through the anchor, and back through at least two openings from the second plurality of openings;
wherein the sealing plug is tri-folded into substantially an S-shape wherein each fold is aligned substantially parallel with a longitudinal axis of the sealing plug; and
wherein the filament weaves between the anchor and the first plurality of openings in a nonlinear pattern.

28. A tissue puncture sealing device according to claim 27 wherein the sealing plug is folded and the tissue puncture sealing device is in an undeployed configuration.

29. A tissue puncture sealing device according to claim 27 wherein the sealing plug has two legs that form an at least approximately symmetrical shape, and wherein the first plurality of openings are in one leg and the second plurality of openings are in another leg.

30. A tissue puncture closure device for partial insertion into and sealing of an internal tissue wall puncture, comprising:
an insertion sheath having first and second ends;
a carrier tube disposed inside the insertion sheath, the carrier tube having first and second ends;
an anchor disposed inside the insertion sheath at the first end thereof, the anchor being disposed outside of the carrier tube at the first end thereof, wherein a portion of the anchor is positioned radially adjacent to an outer diameter of the carrier tube;
a sealing plug disposed inside the carrier tube at the first end thereof:
wherein the sealing plug is folded at least once; and
wherein the tissue puncture closure device is in an undeployed configuration when the tissue puncture closure device is not inserted into a patient;
wherein the sealing plug is tri-folded into an S-shape, wherein each fold is aligned substantially parallel with a longitudinal axis of the sealing plug.

31. A tissue puncture closure device, comprising:
an anchor configured to be inserted through a tissue puncture;
a sealing plug that is compressible; and
a filament configured to couple the anchor and the sealing plug together, the sealing plug being configured to compress when a tension force is applied to the filament;
wherein the sealing plug is generally X-shaped in cross section;
wherein the sealing plug comprises two cross members which form the X-shaped cross section; and
wherein the filament alternately extends through holes in the two cross members in a spiral pattern.

32. A tissue puncture closure device, comprising:
a carrier tube;
an anchor configured to be inserted through a tissue puncture, the anchor comprising a stiff member;
a sealing plug that is compressible, the sealing plug comprising a sponge material; and
a filament configured to couple the anchor and the sealing plug together;
wherein the filament passes through one hole in the sealing plug, though a hole in the anchor, and back Through another hole in the sealing plug, wherein the filament only passes once through each one of the one hole and the another hole; and
wherein the sealing plug is positioned in the carrier tube in an undeployed configuration; and
wherein the one hole is in one leg portion of the sealing plug and the another hole is in another leg portion of the sealing plug.

33. The tissue puncture closure device of claim 32 wherein the sealing plug comprises a first plurality of holes including the one hole in the sealing plug and a second plurality of holes including the another hole in the sealing plug, and wherein the filament passes through the first plurality of holes, through the hole in the anchor, and back through the second plurality of holes.

34. The tissue puncture closure device of claim 32 wherein the sealing plug is folded.

35. The tissue puncture closure device of claim 32 wherein the sealing plug is folded between the one hole in the sealing plug and the another hole in the sealing plug.

36. The tissue puncture closure device of claim 32 wherein the one leg and the another leg form at least two portions that are symmetrical and are folded together, the sealing plug comprising a first plurality of holes in one of the at least two symmetrical portions and a second plurality of holes in another one of the at least two symmetrical portions, the first plurality of holes including the one hole and the second plurality of holes including the another hole, and wherein the filament extends through the first plurality of holes in the one symmetrical portion, through the hole in the anchor, and back through the second plurality of holes in the another symmetrical portion.

37. The tissue puncture closure device of claim 32 wherein the tissue puncture closure device is a vascular puncture closure device, wherein the anchor is configured to be inserted through an opening in a blood vessel and the sealing plug is configured to be positioned opposite the anchor outside of the blood vessel, and wherein the filament is configured to couple the anchor and the sealing plug together across the opening in the blood vessel.

38. A tissue puncture closure device, comprising:
an anchor configured to be inserted through a tissue puncture;
a sealing plug including a first component and a second component, the first component being separate from the second component; and
a filament configured to couple the anchor and the sealing plug together when the anchor and the sealing plug are deployed;
wherein the first component and the second component each have a general U-shape;
wherein the filament passes through one hole in the first component and one hole in the second component before passing through a hole in the anchor and wherein the filament passes through another hole in the first component and another hole in the second component after passing through the hole in the anchor.

39. The tissue puncture closure device of claim 38 wherein the first component and the second component are positioned in an interconnected relationship to each other.

* * * * *